US012616391B2

(12) United States Patent
Guo et al.

(10) Patent No.: US 12,616,391 B2
(45) Date of Patent: May 5, 2026

(54) NEURAL NETWORKS TO DETERMINE RESPIRATION RATES

(71) Applicants: Hewlett-Packard Development Company, L.P., Spring, TX (US); Purdue Research Foundation, West Lafayette, IN (US)

(72) Inventors: Tianqi Guo, San Diego, CA (US); Qian Lin, Palo Alto, CA (US); Jan Allebach, West Lafayette, IN (US)

(73) Assignees: Hewlett-Packard Development Company, L.P., Spring, TX (US); Purdue Research Foundation, West Lafayette, IN (US)

( * ) Notice: Subject to any disclaimer, the term of this patent is extended or adjusted under 35 U.S.C. 154(b) by 426 days.

(21) Appl. No.: 18/246,487

(22) PCT Filed: Oct. 29, 2020

(86) PCT No.: PCT/US2020/058037
§ 371 (c)(1),
(2) Date: Mar. 23, 2023

(87) PCT Pub. No.: WO2022/093244
PCT Pub. Date: May 5, 2022

(65) Prior Publication Data
US 2023/0389817 A1      Dec. 7, 2023

(51) Int. Cl.
*A61B 5/08* (2006.01)
*A61B 5/11* (2006.01)
(Continued)

(52) U.S. Cl.
CPC .......... *A61B 5/0816* (2013.01); *A61B 5/1128* (2013.01); *A61B 5/113* (2013.01);
(Continued)

(58) Field of Classification Search
None
See application file for complete search history.

(56) References Cited

U.S. PATENT DOCUMENTS 9,805,255 B2    10/2017  Yang et al.
10,136,856 B2   11/2018  Tzvieli et al.
(Continued)

FOREIGN PATENT DOCUMENTS

CN      104665768 A     6/2015
CN      109620156 A     4/2019
(Continued)

OTHER PUBLICATIONS

Chatterjee, Avishek, et al. "Real-time visual respiration rate estimation with dynamic scene adaptation." 2016 IEEE 16th International Conference on Bioinformatics and Bioengineering (BIBE). IEEE, 2016. (Year: 2016).*
(Continued)

*Primary Examiner* — Michelle M Entezari Hausmann
(74) *Attorney, Agent, or Firm* — Quarles & Brady LLP

(57) ABSTRACT
In some examples, a non-transitory computer-readable medium stores executable code, which, when executed by a processor, causes the processor to receive a video of at least part of a human torso, use a neural network to produce multiple vector fields based on the video, the multiple vector fields representing movement of the human torso, and determine a respiration rate of the human torso using the multiple vector fields.

18 Claims, 6 Drawing Sheets

(51) Int. Cl.

| | |
|---|---|
| *A61B 5/113* | (2006.01) |
| *G06V 10/26* | (2022.01) |
| *G06V 10/82* | (2022.01) |
| *G06V 40/10* | (2022.01) |
| *G06V 40/20* | (2022.01) |

(52) U.S. Cl.
CPC ............ *G06V 10/273* (2022.01); *G06V 10/82* (2022.01); *G06V 40/10* (2022.01); *G06V 40/20* (2022.01)

(56) References Cited

U.S. PATENT DOCUMENTS

| | | | | |
|---|---|---|---|---|
| 10,423,830 | B2 | 9/2019 | Chalom et al. | |
| 10,643,081 | B2 | 5/2020 | Silberschatz et al. | |
| 11,631,193 | B1 * | 4/2023 | Akbas .................... | G06N 3/045 |
| | | | | 382/103 |
| 11,783,500 | B2 * | 10/2023 | Casser ..................... | G06T 3/18 |
| | | | | 382/100 |
| 2014/0236036 | A1 | 8/2014 | De Haan et al. | |
| 2017/0347061 | A1 | 11/2017 | Wang et al. | |
| 2018/0000382 | A1 * | 1/2018 | Chatterjee .............. | A61B 5/113 |
| 2018/0033144 | A1 * | 2/2018 | Risman .................. | G06V 10/82 |
| 2019/0183444 | A1 * | 6/2019 | Castillo ..................... | G06T 7/37 |
| 2020/0258227 | A1 | 8/2020 | Liao et al. | |
| 2021/0100492 | A1 * | 4/2021 | Knight ................. | A61B 5/7264 |
| 2021/0158543 | A1 * | 5/2021 | Sun ........................ | G06T 7/0012 |
| 2021/0350549 | A1 * | 11/2021 | Lu ........................... | G06V 10/82 |
| 2021/0374925 | A1 * | 12/2021 | Finlayson ............ | G06V 10/454 |
| 2021/0397886 | A1 * | 12/2021 | Chen .................... | G06N 3/0475 |
| 2022/0012815 | A1 * | 1/2022 | Kearney .............. | G06N 3/0475 |
| 2022/0014723 | A1 * | 1/2022 | Pandey ..................... | G06T 5/60 |
| 2022/0092791 | A1 * | 3/2022 | Dougherty ................ | G06T 7/62 |
| 2022/0101537 | A1 * | 3/2022 | Sun ....................... | G06T 3/4046 |
| 2022/0122717 | A1 * | 4/2022 | Budz ...................... | G16H 30/40 |
| 2023/0126640 | A1 * | 4/2023 | Novosad .............. | A61B 5/7267 |
| | | | | 382/128 |
| 2023/0146134 | A1 * | 5/2023 | Selviah ................ | G06V 20/653 |
| | | | | 345/419 |

FOREIGN PATENT DOCUMENTS

| | | | | |
|---|---|---|---|---|
| CN | 111882538 | A * | 11/2020 | ............ G06N 3/045 |
| WO | 2009/128000 | A1 | 10/2009 | |

OTHER PUBLICATIONS

CN 111882538 A [Machine Translation] (Year: 2020).*

Wolthaus, Jochem WH, et al. "Reconstruction of a time-averaged midposition CT scan for radiotherapy planning of lung cancer patients using deformable registration a." Medical physics 35.9 (2008): 3998-4011. (Year: 2008).*

Mateu-Mateus, Marc, Federico Guede-Fernandez, Miguel Angel Garcia-Gonzalez, Juan José Ramos-Castro, and Mireya Fernández-Chimeno. "Camera-based method for respiratory rhythm extraction from a lateral perspective." IEEE access 8 (2020): 154924-154939. (Year: 2020).*

Guo, Tianqi, Qian Lin, and Jan Allebach. "Remote estimation of respiration rate by optical flow using convolutional neural networks." Electronic Imaging 33 (2021): 1-11. (Year: 2021).*

Brieva J. et al., "A Contactless Respiratory Rate Estimation Method Using a Hermite Magnification Technique and Convolutional Neural Networks", Journals, Applied Sciences, vol. 10, No. 2, Jan. 15, 2020. pp. 1-20.

Zhan, et al., "Revisiting motion-based respiration measurement from videos", 2020 42nd Annual International Conference of the IEEE Engineering in Medicine & Biology Society (EMBC), , Jul. 20, 2020, pp. 5909-5912.

\* cited by examiner

100

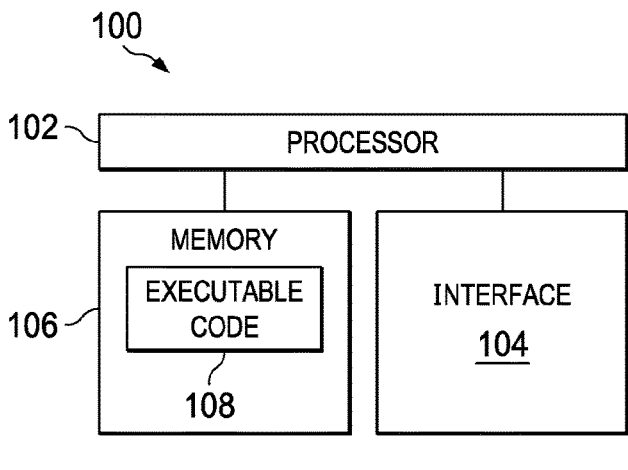

204 — RECEIVE VIDEO

206 — PERFORM CONVOLUTIONAL NEURAL NETWORKS TO DETERMINE OPTICAL FLOW

216 — PERFORM CONVOLUTIONAL NEURAL NETWORKS FOR PERSON SEGMENTATION

208 — PRODUCE VECTOR FIELD

218 — PRODUCE BOUNDING BOX OR SEGMENTATION MASK

210 — PRODUCE RESPIRATION SIGNAL

212 — CALCULATE AVERAGE VALUE

214 — THRESHOLD ANALYSIS TIME REACHED?     NO

YES

220 — PERFORM FREQUENCY ANALYSIS

222 — DESIGNATE RESPIRATION RATE

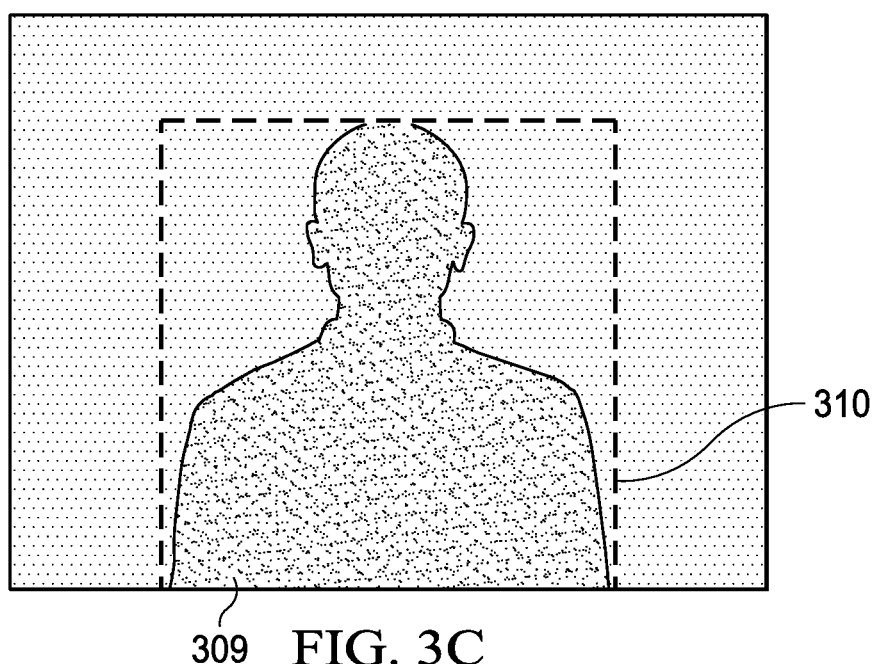
309 FIG. 3C
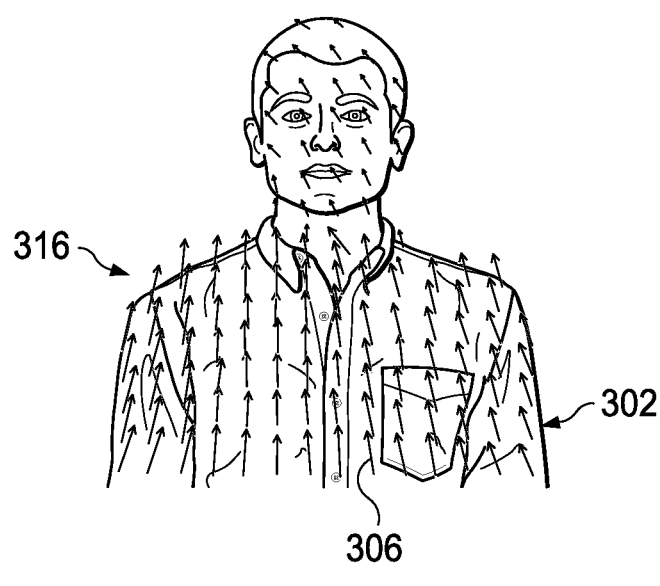
FIG. 3D

600

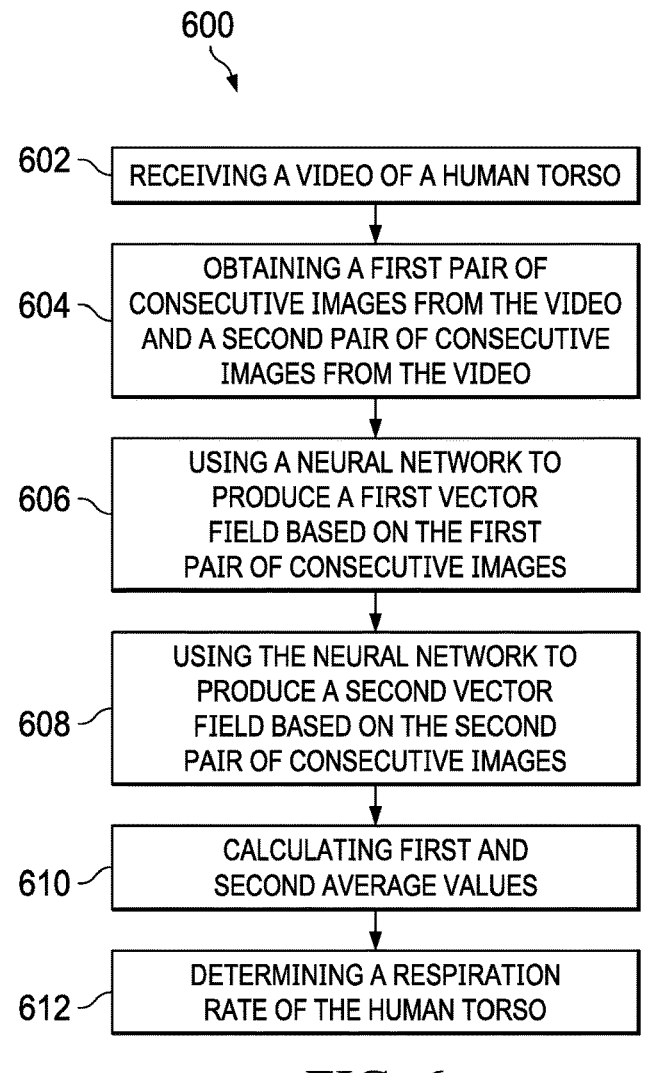

602 — RECEIVING A VIDEO OF A HUMAN TORSO

604 — OBTAINING A FIRST PAIR OF CONSECUTIVE IMAGES FROM THE VIDEO AND A SECOND PAIR OF CONSECUTIVE IMAGES FROM THE VIDEO

606 — USING A NEURAL NETWORK TO PRODUCE A FIRST VECTOR FIELD BASED ON THE FIRST PAIR OF CONSECUTIVE IMAGES

608 — USING THE NEURAL NETWORK TO PRODUCE A SECOND VECTOR FIELD BASED ON THE SECOND PAIR OF CONSECUTIVE IMAGES

610 — CALCULATING FIRST AND SECOND AVERAGE VALUES

612 — DETERMINING A RESPIRATION RATE OF THE HUMAN TORSO

FIG. 6

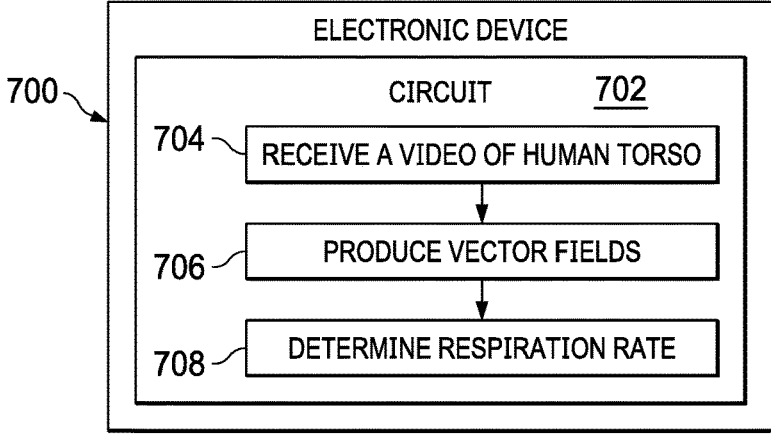

700

ELECTRONIC DEVICE

CIRCUIT    702

704 — RECEIVE A VIDEO OF HUMAN TORSO

706 — PRODUCE VECTOR FIELDS

708 — DETERMINE RESPIRATION RATE

FIG. 7

NEURAL NETWORKS TO DETERMINE RESPIRATION RATES

BACKGROUND

The human respiration rate is frequently measured in a variety of contexts to obtain information regarding pulmonary, cardiovascular, and overall health. For example, doctors often measure respiration rate in clinics and hospitals.

BRIEF DESCRIPTION OF THE DRAWINGS

Various examples will be described below referring to the following figures:

FIG. 1 is a block diagram of an electronic device to determine respiration rates using neural networks, in accordance with various examples.

FIG. 2 is a flow diagram of a method to determine respiration rates using neural networks, in accordance with various examples.

FIGS. 3A-3F are a process flow to determine respiration rates using neural networks, in accordance with various examples.

FIG. 6 is a flow diagram of a method to determine respiration rates using neural networks, in accordance with various examples.

FIG. 7 is a block diagram of an electronic device to determine respiration rates using neural networks, in accordance with various examples.

DETAILED DESCRIPTION

Figure 3A:
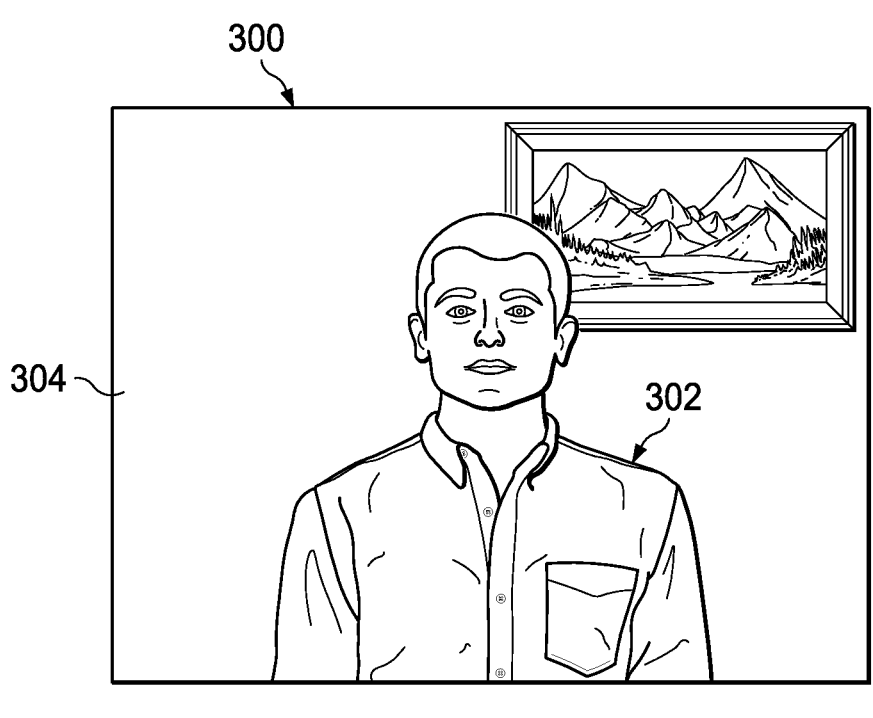

Various techniques and devices can be used to measure respiration rate. Many such techniques and devices operate based on the fact that inhalation and exhalation during respiration cycles are associated with pulmonary volume changes as well as the expansion and contraction of the anteroposterior diameters of the rib cage and abdomen. Accordingly, common techniques for measuring respiration rate include visual observation, impedance pneumography, and respiration belts that include accelerometers, force sensors, and pressure sensors that sense motions of the chest wall.

These approaches for measuring respiration rate have multiple disadvantages. For example, because the subject is present in person for her respiration rate to be measured, she is at risk for the transmission of pathogens via respiration rate monitoring devices or via the air, and she spends time and money traveling to and from the clinic at which her respiration rate is to be measured. Techniques for measuring respiration rate from a remote location using a camera suffer from poor accuracy, particularly in challenging conditions (e.g., in poorly-lit environments).

This disclosure describes various examples of a technique for using a camera to remotely measure respiration rate in a variety of challenging conditions. In examples, the technique includes receiving a video of a human torso (e.g., including the shoulders, chest, back, and/or abdomen of a subject), such as a live-stream video via a network interface or a stored video via a peripheral interface. Other body parts, such as the head, also may be used, although the accuracy may be less than if the shoulders, chest, back, and/or abdomen are used. The term human torso, as used herein, may include any such body part(s), including the head, shoulders, chest, back, and/or abdomen of a subject. The technique includes applying multiple pairs of consecutive images from the video to a convolutional neural network (CNN) to produce multiple vector fields, each vector field corresponding to a different pair of consecutive images from the video and indicating movement (e.g., respiratory movement) between the consecutive images in the pair. In some examples, images from the video may be applied to another CNN to produce segmentation masks, and these segmentation masks may be applied to corresponding vector fields to filter vectors in the vector fields that do not correspond to the human torso. For instance, multiplying a vector field by a segmentation mask may cause the vectors corresponding to a background or to another subject(s) in the video to be removed from the vector field.

The technique also includes, for each vector field, calculating an average horizontal value using the horizontal components of some or all of the vectors in the vector field, and calculating an average vertical value using the vertical components of some or all of the vectors in the vector field. The greater of the average horizontal and average vertical values is selected as an average value that is representative of respiratory movement of the subject. These average values may be plotted over a target length of time (e.g., 60 seconds), for example, on a graph of time versus spatial displacement. The set of average values may be converted to the frequency domain to produce a frequency distribution, and the dominant frequency in the frequency distribution (e.g., the frequency with the greatest normalized coefficient) may be designated as the respiration rate of the subject in the video. The CNN used to produce the vector fields may be trained using data sets having various lighting conditions, subjects with different types of clothing, etc., to mitigate the effect of these variables on the accuracy of the determined respiratory rate.

FIG. 1 is a block diagram of an electronic device to determine respiration rates using neural networks, in accordance with various examples. In particular, FIG. 1 shows an electronic device 100, such as a personal computer, a workstation, a server, a smartphone, a distributed device (e.g., one or more personal computers in communication with a server providing cloud-based computation services), etc. In examples, the electronic device 100 includes a processor 102, an interface 104 coupled to the processor 102, and a memory 106 coupled to the processor 102. The memory 106 includes executable code 108. In some examples, a microcontroller or other suitable type of controller may be substituted for the processor 102 and/or the memory 106. The processor 102 accesses the executable code 108 in the memory 106 and executes the executable code 108. Upon execution, the executable code 108 causes the processor 102 to perform some or all of the actions attributed herein to the processor 102 and/or to the electronic device 100. In examples, the executable code 108 includes instructions to implement some or all of the techniques described herein, such as the methods, process flows, and neural networks described below with reference to FIGS. 2-7. In addition, the scope of this disclosure is not limited to electronic devices in which processors execute executable code to perform the techniques described herein. Rather, other types of electronic devices, such as field programmable gate arrays and application-specific integrated circuits, also may be used.

The interface 104 may be any suitable type of interface. In some examples, the interface 104 is a network interface through which the electronic device 100 is able to access a network, such as the Internet, a local area network, a wide local area network, a virtual private network, etc. In some examples, the interface 104 is a peripheral interface, meaning that through the interface 104, the electronic device 100 is able to access a peripheral device, such as a camera (e.g., a webcam), a removable or non-removable storage device (e.g., a memory stick, a compact disc, a portable hard drive), etc. In some examples, the electronic device 100 includes multiple interfaces 104, with each interface 104 to facilitate access to a different peripheral device or network. Through the interface 104, the electronic device 100 is able to receive a video, such as a live-stream video or a stored, pre-recorded video. As described below, the electronic device 100 may use neural networks to determine the respiration rate of a human subject in the video.

FIG. 2 is a flow diagram of a method 200 to determine respiration rates using neural networks, in accordance with various examples. FIGS. 3A-3F form a process flow to determine respiration rates using neural networks, in accordance with various examples. The method 200 of FIG. 2 and the process flow of FIGS. 3A-3F are now described in parallel, with occasional reference to FIG. 1.

The method 200 includes receiving a video (204). More specifically, the processor 102 may receive a video by way of the interface 104. The video may be a live-stream video or a pre-recorded video and may be received from any suitable source. In some examples, the processor 102 receives a live-stream video via a network interface 104, such as via the Internet from a remotely located webcam. In examples, the processor 102 receives a pre-recorded video from a storage device, such as a compact disc, a thumb drive, or a portable hard drive, via a peripheral interface 104. In examples, the processor 102 receives a pre-recorded video via the network interface 104. Such variations are contemplated and included in the scope of this disclosure. FIG. 3A depicts a representative image (or frame) of a video 300, such as the video that may be received via the interface 104 in 204 of method 200. The video 300 includes a human subject, and more specifically, a human torso 302 whose respiration rate is to be measured. The video 300 also includes a background 304, which may include any type of background such as walls, furniture, pets, books, electronics, other humans, etc. Different examples of the video 300 may have various types and qualities of lighting, and the human torso 302 may be clothed with different types of clothing. Other variations are contemplated and included in the scope of this disclosure.

The method 200 includes using a convolutional neural network (CNN) to determine an optical flow of the human torso 302 (206). As used herein, the term optical flow refers to the movement of the human torso 302 as recorded in the video 300 and as depicted by the pixels of the video 300. The CNN of 206 may be encoded in the executable code 108 and may be executed by the processor 102. When executing the CNN of 206, the processor 102 may receive pairs of consecutive images (or frames) of the video 300 as inputs. In addition, when executing the CNN of 206, the processor 102 may output a vector field at 208 for each pair of consecutive images received. Thus, for example, the processor 102, when executing the CNN of 206, may receive the first and second frames of the video 300 and may output one vector field based on the first and second frames.

Figure 3B:
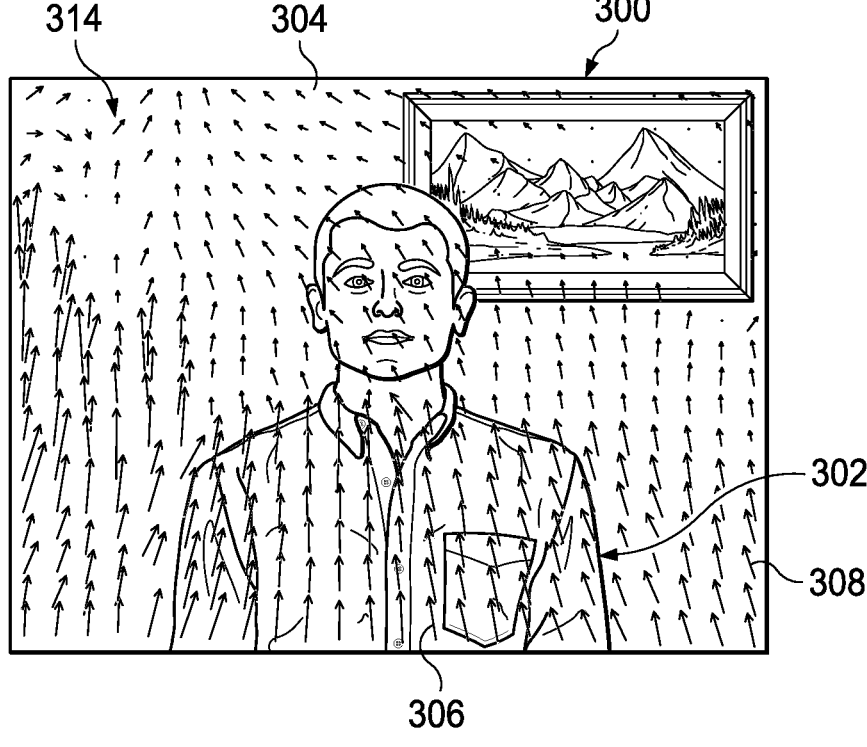

As used herein, a vector field refers to a set of vectors (e.g., one vector per pixel) that represent the image deformation of a second image in a pair of images from the video 300 relative to the first image in the pair. Stated another way, the vector field includes a set of vectors (e.g., one vector for each pixel) that represent movement of the human torso 302 between two frames in a pair of frames. Thus, a vector field provides information regarding the respiratory movement of the human torso 302. FIG. 3B shows an example vector field 314, which includes vectors 306 (representing movement of the human torso 302) and vectors 308 (representing background movement or noise). Each vector in the vector field 314 includes horizontal and vertical components, with the horizontal component indicating movement in the horizontal direction and the vertical component indicating movement in the vertical direction.

The CNN may be trained using appropriate data sets that correlate video frames in various conditions (e.g., different lighting conditions, different clothing, different colors, etc.) to specific vector fields. Although the architecture of the CNN may vary, in some examples, the CNN includes an encoder-decoder architecture that comprises a contraction portion and an expansion portion. The contraction portion may extract feature representations from each pair of images of the video 300 and may reduce spatial resolution through consecutive convolutions, activation, and pooling layers. A cross-correlation layer may subsequently be used to recover the spatial correspondence between the pair of images. The expansion portion may receive feature maps from the contraction portion as input, may predict local deformation vectors, may recover spatial resolution by consecutive upconvolution and unpooling layers, and may preserve fine local details. Such preservation of local details may include a dense prediction of displacement at each pixel, with a finer resolution of spatial displacement gradient and better-distinguished boundaries of a moving foreground (e.g., the human torso) versus a stationary background (e.g., the environment behind the human torso).

The method 200 includes using another CNN (216) to produce a bounding box or a segmentation mask (218). The CNN in 216 may be encoded in the executable code 108 and may be executed by the processor 102. When executing the CNN in 216, the processor 102 may receive as input an image of the video 300, and it may output a bounding box or a segmentation mask, either of which may be used to filter out vector field vectors that are in the background of the human torso 302. FIG. 3C depicts a sample segmentation mask 309 and a sample bounding box 310. The CNN may be trained using appropriate data sets that correlate video frames in various conditions (e.g., different lighting conditions, different clothing, different colors, etc.) to specific bounding boxes and/or segmentation masks.

The method 200 includes using the bounding box or segmentation mask to filter out background vectors (e.g., vectors representing background movement or background noise) from the vector field produced in 208 (210), thus producing a respiration signal. For example, the segmentation mask 309 may be used to filter out the background vectors 308 from the vector field 314. The segmentation mask 309 would not, however, cause vectors 306 to be removed. Similarly, in examples, the bounding box 310 may be used to filter out at least some of the background vectors 308 from the vector field 314, but the bounding box 310 would not cause vectors 306 (and, in examples, some of the vectors 308 circumscribing the human torso 302) to be removed. In examples, the segmentation mask 309 or the bounding box 310 is multiplied by the vector field 314 to produce the respiration signal (210), which is a modified version of the vector field 314. FIG. 3D depicts an example respiration signal 316, which includes the human torso 302 and vectors 306 corresponding to the movement (including respiratory movement) of the human torso 302. The segmentation mask 309, rather than the bounding box 310, is used to produce the specific example of FIG. 3D.

The method 200 includes calculating an average value of the vectors 306 in the respiration signal 316 (212). As explained above, each vector 306 includes horizontal and vertical components. In examples, the processor 102 averages some or all of the horizontal components of the vectors 306 in the respiration signal 316 to produce an average horizontal value. In examples, the processor 102 averages some or all of the vertical components of the vectors 306 in the respiration signal 316 to produce an average vertical value. Because videos may be recorded in differing orientations (e.g., a smartphone camera may record a video in landscape or portrait format), the average horizontal value may actually be a vertical value, and the average vertical value may actually be a horizontal value. During respiration, the human torso 302 generally moves in a vertical direction. Thus, to identify the true vertical direction, the processor 102 may compare the average horizontal value with the average vertical value to identify the greater value, and the processor 102 may designate this greater value as the true average vertical value with the lesser value being designated as the true average horizontal value. The processor 102 may designate the true average vertical value as the average value of 212 in FIG. 2, and the processor 102 may discard the true average horizontal value. As 214 indicates, 204, 206, 208, 216, 218, 210, and 212 are iteratively repeated until a threshold analysis time is reached. For example, the processor 102 may iteratively repeat the portions of the method 200 described above until 15 seconds, 30 seconds, 45 seconds, 60 seconds, etc. have elapsed, meaning that average values have been obtained for 15 seconds of video 300, 30 seconds of video 300, 45 seconds of video 300, 60 seconds of video 300, etc. In examples, at least 60 seconds of average values are obtained for enhanced accuracy of respiration rate calculations. In some examples, rather than determining the true average horizontal and vertical values and selecting the greater of the two, the processor 102 may perform a fast Fourier transform (FFT) to convert the horizontal vector components and the vertical vector components to the frequency domain, and the processor 102 may then identify the dominant frequencies for each of the FFT conversions, designating the greater of the two dominant frequencies as the respiration rate of the human torso.

Figure 3E:
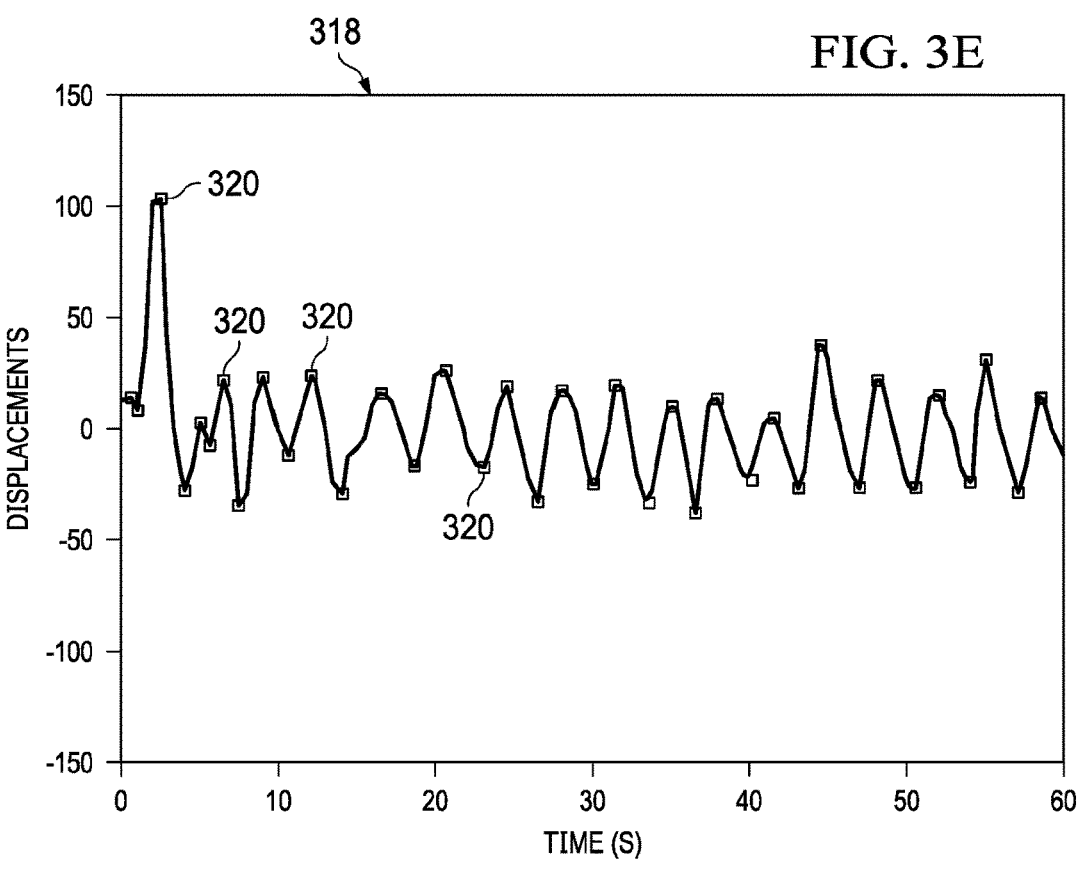
Figure 3F:
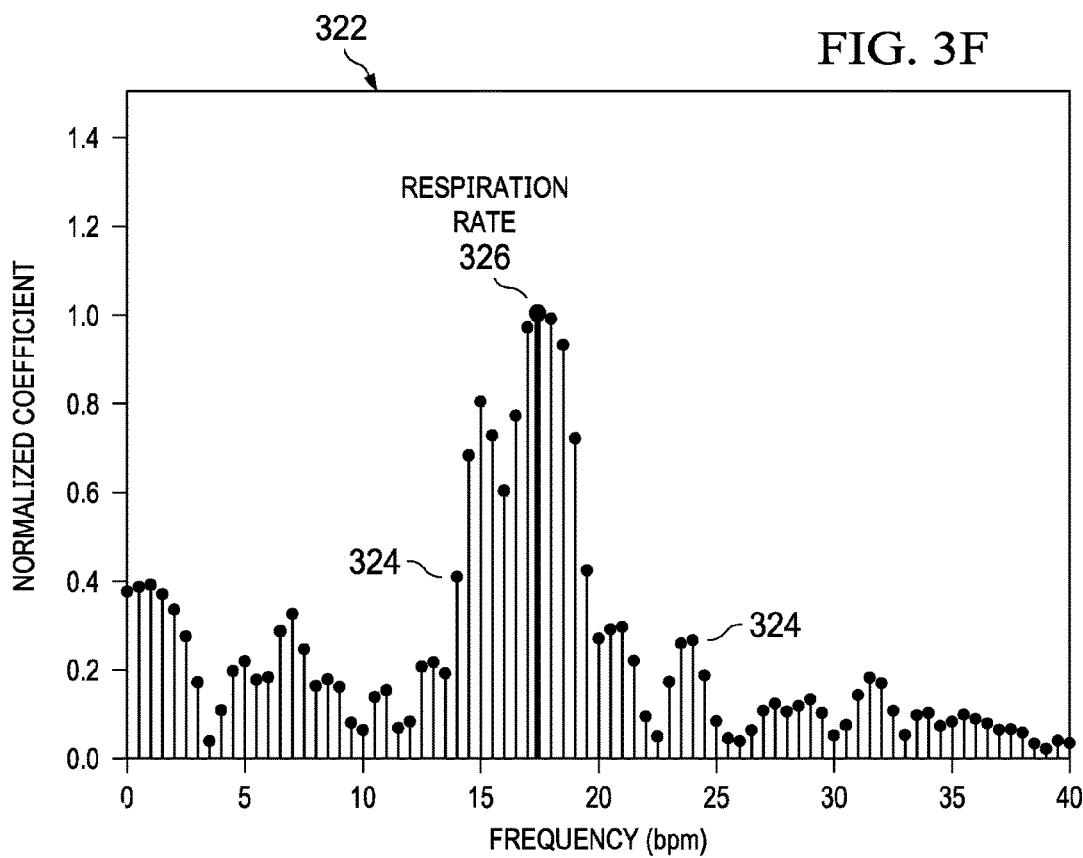

FIG. 3E is a graph 318 depicting example average values obtained over the course of 60 seconds. The x-axis indicates time, and the y-axis indicates spatial displacement. The graph 318 includes a set of average values 320, each of which is calculated by the processor 102 at 212 in FIG. 2. The method 200 includes performing a frequency analysis on the set of average values (220), for example, by the processor 102 performing a fast Fourier transform (FFT) on the set of average values 320 to convert the set of average values 320 to the frequency domain. In examples, FFT is performed after padding, windowing (e.g., Han windowing), and mean subtraction (e.g., detrending) of the set of average values 320. FIG. 3F is a graph 322 including frequencies 324 of a frequency distribution. The graph 322 includes an x-axis for frequency (in breaths per minute) and the y-axis includes a normalized coefficient for the frequencies. The frequencies 324 include a dominant frequency 326. The processor 102 may designate the dominant frequency 326 as the respiration rate of the human torso 302 (222). In examples, prior to identifying and designating the dominant frequency 326 as the respiration rate of the human torso 302, the processor 102 may filter the frequencies 324 to remove frequencies outside of a target frequency range, with the target frequency range corresponding to a normal respiration rate (e.g., 2 breaths per minute to 40 breaths per minute).

Figure 4:
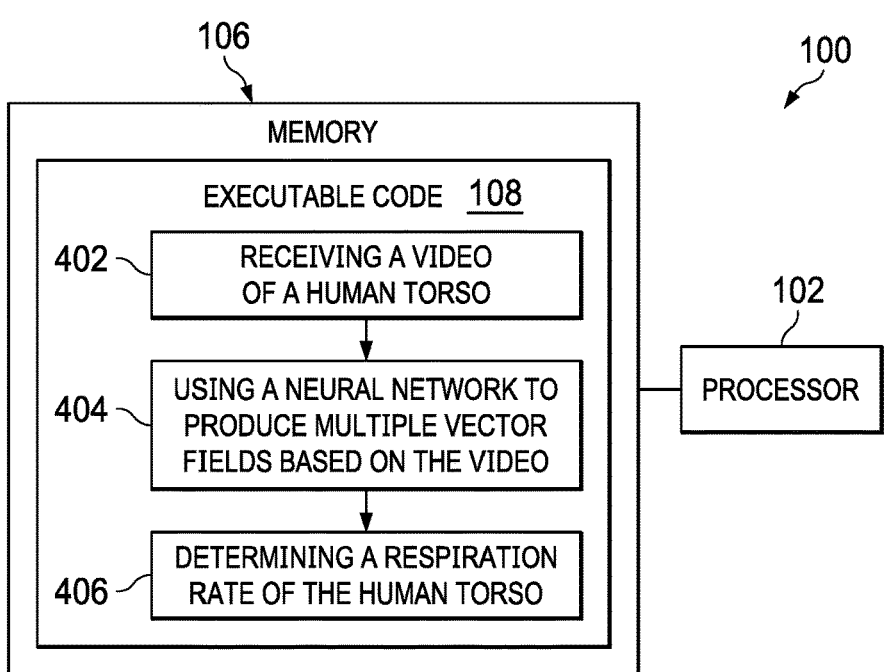
FIGS. 4 and 5 are block diagrams of electronic devices to determine respiration rates using neural networks, in accordance with various examples.
Figure 5:
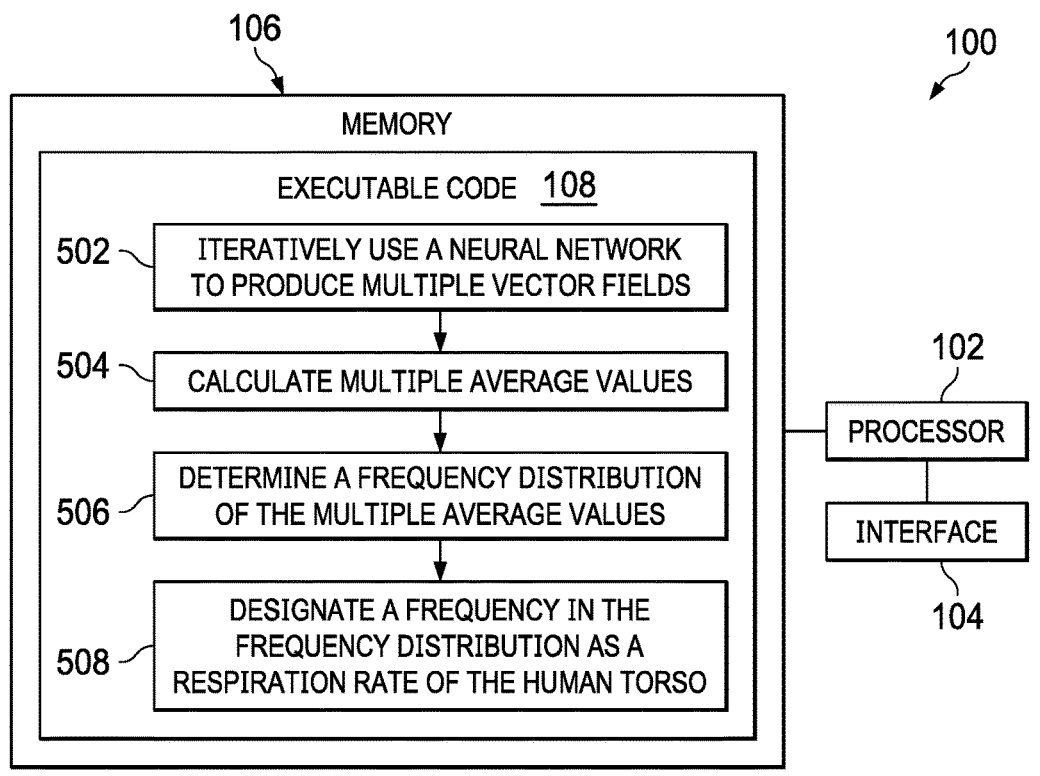

FIGS. 4 and 5 are block diagrams of electronic devices to determine respiration rates using neural networks, in accordance with various examples. FIG. 4 shows an electronic device 100 including the processor 102, the memory 106 coupled to the processor 102, and executable code 108 stored in the memory 106. FIG. 5 shows an electronic device 100 that includes the processor 102, the interface 104 coupled to the processor 102, and the memory 106 coupled to the processor 102. The memory 106 stores executable code 108. FIG. 6 is a flow diagram of a method 600 to determine respiration rates using neural networks, in accordance with various examples. The techniques shown in the executable codes 108 of FIGS. 4 and 5 and in the method 600 of FIG. 6 are variations of the method 200 and the process flow of FIGS. 3A-3F, which are described in detail above, and thus they are not described in detail for the sake of brevity. The executable code 108 of FIG. 4 includes instructions for receiving a video of at least part of a human torso (402). The executable code 108 of FIG. 4 includes using a neural network to produce multiple vector fields based on the video, the multiple vector fields representing movement of the human torso (404). The executable code 108 of FIG. 4 includes determining a respiration rate of the human torso using the multiple vector fields (406).

The executable code 108 of FIG. 5 includes instructions for iteratively using a neural network to produce multiple vector fields, each vector field indicative of movement of the human torso between a different pair of consecutive images of the video (502). The executable code 108 of FIG. 5 includes calculating multiple average values, each average value calculated using vectors of a different one of the multiple vector fields (504). The executable code 108 of FIG. 5 includes determining a frequency distribution of the multiple average values (506). The executable code 108 of FIG. 5 includes designating a frequency in the frequency distribution as a respiration rate of the human torso (508).

The method 600 of FIG. 6 includes receiving a video of at least part of a human torso (602). The method 600 includes obtaining a first pair of consecutive images from the video and a second pair of consecutive images from the video (604). The method 600 includes using a neural network to produce a first vector field based on the first pair of consecutive images, the first vector field representative of movement of the human torso (606). The method 600 includes using the neural network to produce a second vector field based on the second pair of consecutive images, the second vector field representative of movement of the human torso (608). The method 600 includes calculating first and second average values using the first and second vector fields, respectively (610). The method 600 includes determining a respiration rate of the human torso using the first and second average values (612).

FIG. 7 is a block diagram of an electronic device to determine respiration rates using neural networks, in accordance with various examples. Specifically, FIG. 7 shows an electronic device 700 that includes a circuit 702. The circuit 702 includes multiple circuit components, such as digital logic components, analog circuit components, or a combination thereof. In some examples, the circuit 702 is an application-specific integrated circuit. In some examples, the circuit 702 is a field programmable gate array that has been programmed using a suitable netlist generated using a hardware description language (HDL) description that implements some or all of the methods, process flows, and/or neural networks described herein. For instance, as shown in FIG. 7, the circuit 702 is to receive a video of at least part of a human torso (704), use a neural network to produce multiple vector fields based on the video (706), the multiple vector fields representing movement of the human torso, and determine a respiration rate of the human torso using the multiple vector fields (708).

The above discussion is meant to be illustrative of the principles and various examples of the present disclosure. Numerous variations and modifications to this disclosure are contemplated. It is intended that the following claims be interpreted to embrace all such variations and modifications.

What is claimed is:

1. A non-transitory computer-readable medium storing executable code, which, when executed by a processor, causes the processor to:

receive a video of at least part of a human torso;

use a first neural network to produce multiple vector fields based on the video, the multiple vector fields representing movement of the human torso;

determine a respiration rate of the human torso using the multiple vector fields;

use a second neural network and the video to produce a segmentation mask; and multiply the segmentation mask by one of the multiple vector fields to remove vectors in the one of the multiple vector fields, the removed vectors corresponding to a background to the human torso.

2. The computer-readable medium of claim 1, wherein the executable code, when executed by the processor, causes the processor to:

determine an average value of multiple vectors in each of the multiple vector fields;

determine a frequency distribution of the average values; and designate the dominant frequency in the frequency distribution as the respiration rate.

3. The computer-readable medium of claim 2, wherein the executable code, when executed by the processor, causes the processor to:

determine an average horizontal value of horizontal components of multiple vectors in at least one of the multiple vector fields;

determine an average vertical value of vertical components of multiple vectors in the at least one of the multiple vector fields; and designate the greater of the average horizontal value and the average vertical value as the average value.

4. The computer-readable medium of claim 1, wherein the first neural network includes a contraction portion that is to cause the processor to reduce spatial resolution of images in the video, and wherein the first neural network includes an expansion portion that is to cause the processor to recover spatial resolution of the images.

5. The computer-readable medium of claim 1, wherein the first neural network is a convolutional neural network.

6. The computer-readable medium of claim 1, wherein the second neural network is a convolutional neural network.

7. An electronic device, comprising:

an interface to receive a video of at least part of a human torso;

a memory storing executable code; and a processor coupled to the interface and to the memory, wherein, as a result of executing the executable code, the processor is to:

iteratively use a neural network to produce multiple vector fields, each vector field indicative of movement of the human torso between a different pair of consecutive images of the video;

calculate multiple average values, each average value calculated using vectors of a different one of the multiple vector fields;

determine a frequency distribution of the multiple average values; and designate a frequency in the frequency distribution as a respiration rate of the human torso.

8. The electronic device of claim 7, wherein the interface is a network interface, and wherein the video is a live-stream video.

9. The electronic device of claim 7, wherein the interface is a peripheral interface.

10. The electronic device of claim 7, wherein the frequency is the dominant frequency in the frequency distribution.

11. The electronic device of claim 7, wherein the neural network is a convolutional neural network.

12. The electronic device of claim 7, further comprising a camera to capture the video.

13. The electronic device of claim 12, wherein the electronic device is a smartphone.

14. A method, comprising:

receiving a video of at least part of a human torso;

obtaining a first pair of consecutive images from the video and a second pair of consecutive images from the video;

using a neural network to produce a first vector field based on the first pair of consecutive images, the first vector field representative of movement of the human torso;

using the neural network to produce a second vector field based on the second pair of consecutive images, the second vector field representative of movement of the human torso;

calculating first and second average values using the first and second vector fields, respectively; and determining a respiration rate of the human torso using the first and second average values.

15. The method of claim 14, wherein receiving the video comprises receiving a live-stream video via a network interface.

16. The method of claim 14, wherein calculating the first average value using the first vector field comprises:

calculating an average horizontal value of horizontal components of multiple vectors in the first vector field;

calculating an average vertical value of vertical components of the multiple vectors in the first vector field; and designating the greater of the average horizontal value and the average vertical value as the first average value.

17. The method of claim 14, comprising:

using a second neural network and the video to produce a segmentation mask; and filtering the first vector field using the segmentation mask prior to calculating the first average value.

18. The method of claim 14, wherein determining the respiration rate using the first and second average values includes determining a frequency distribution of the first and second average values and designating the dominant frequency in the frequency distribution as the respiration rate.

* * * * *